United States Patent
Noda et al.

(10) Patent No.: US 10,667,819 B2
(45) Date of Patent: Jun. 2, 2020

(54) DELIVERY ASSEMBLY FOR RESILIENT TISSUE CLAMP

(71) Applicant: Insightra Medical, Inc., Irvine, CA (US)

(72) Inventors: Wayne A. Noda, Irvine, CA (US); Brendan Cummings, Irvine, CA (US); Daniel Hyman, Irvine, CA (US)

(*) Notice: Subject to any disclaimer, the term of this patent is extended or adjusted under 35 U.S.C. 154(b) by 781 days.

(21) Appl. No.: 14/997,733

(22) Filed: Jan. 18, 2016

(65) Prior Publication Data

US 2017/0202555 A1    Jul. 20, 2017

(51) Int. Cl.
| | |
|---|---|
| A61B 17/04 | (2006.01) |
| A61B 17/12 | (2006.01) |
| A61B 17/00 | (2006.01) |
| A61B 17/064 | (2006.01) |
| A61B 90/00 | (2016.01) |

(52) U.S. Cl.
CPC ......... *A61B 17/12013* (2013.01); *A61B 2017/00818* (2013.01); *A61B 2017/00876* (2013.01); *A61B 2017/0641* (2013.01); *A61B 2017/12018* (2013.01); *A61B 2090/031* (2016.02)

(58) Field of Classification Search
CPC ....... A61B 17/10; A61B 17/115; A61B 17/12; A61B 17/128; A61B 17/1285; A61B 17/12009; A61B 17/12013; A61B 2017/12018; A61B 1/00131; A61B 1/00137; A61B 1/0014
USPC .......................................... 606/139
See application file for complete search history.

(56) References Cited

U.S. PATENT DOCUMENTS

| | | | |
|---|---|---|---|
| 4,517,090 A | 5/1985 | Kersten et al. | |
| 4,548,201 A | 10/1985 | Yoon | |
| 4,820,304 A | 4/1989 | Depel et al. | |
| 5,776,187 A * | 7/1998 | Krueger | A61F 2/2427 |
| | | | 623/2.11 |
| 5,972,009 A | 10/1999 | Fortier et al. | |

(Continued)

FOREIGN PATENT DOCUMENTS

| | | |
|---|---|---|
| WO | 1996025886 A9 | 8/1996 |
| WO | 1996029965 A1 | 10/1996 |

OTHER PUBLICATIONS

"6 Shooter Universal Saeed Multi-Band Ligator", Cook Medical, https://www.cookmedical.com/products/esc_mbl_webds/.
Wayne A. Noda, "Delivery Assembly for Resilient Tissue Clamp", file history of related U.S. Appl. No. 13/898,896, filed May 21, 2013.

(Continued)

*Primary Examiner* — Melanie R Tyson
(74) *Attorney, Agent, or Firm* — Mark A. Pitchford; Eric B. Fugett; Pitchford Fugett, PLLC

(57) ABSTRACT

A delivery assembly includes a sleeve that fits snugly over a main endoscope over a distal end of the endoscope. A cylindrical carrier projects distally away from the sleeve and can carry one or more resilient tissue compression rings in a stretched configuration. A push ring is slidably disposed on the carrier, and an actuator is connected to the push ring. The actuator extends through the carrier, around a distal end of the carrier, and to the push ring to connect thereto such that when the actuator is pulled proximally, the push ring is urged distally on the carrier to push at least one compression ring off the carrier, at which point the compression ring is relaxed to assume a small configuration and clamp target tissue. The actuator may include a distal segment made of a flat ribbon.

3 Claims, 4 Drawing Sheets

(56) References Cited

U.S. PATENT DOCUMENTS

| | | | |
|---|---|---|---|
| 5,976,158 A | 11/1999 | Adams et al. | |
| 5,980,537 A | 11/1999 | Ouchi | |
| 6,007,551 A * | 12/1999 | Peifer | A61B 17/12013 |
| | | | 606/139 |
| 6,849,078 B2 | 2/2005 | Durgin et al. | |
| 7,189,247 B1 | 3/2007 | Zirps et al. | |
| 7,641,652 B2 | 1/2010 | Coe et al. | |
| 7,766,020 B2 | 8/2010 | Chininis et al. | |
| 7,819,895 B2 | 10/2010 | Ginn et al. | |
| 8,062,308 B2 | 11/2011 | Noda et al. | |
| 8,647,352 B2 | 2/2014 | Noda et al. | |
| 2002/0072757 A1 * | 6/2002 | Ahmed | A61B 17/12013 |
| | | | 606/139 |
| 2005/0192629 A1 | 9/2005 | Saadat et al. | |
| 2007/0225762 A1 | 9/2007 | LaBombard | |
| 2009/0105728 A1 * | 4/2009 | Noda | A61B 17/12013 |
| | | | 606/139 |
| 2009/0157101 A1 | 6/2009 | Reyes et al. | |

OTHER PUBLICATIONS

Wayne A. Noda, "Devices and Methods for Securing Tissue", file history of related U.S. Appl. No. 14/714,730, filed May 18, 2015.

Wayne A. Noda, Stephen Graham Bell, "Devices and Methods for Securing Tissue", file history of related U.S. Appl. No. 14/043,038, filed Oct. 1, 2013.

Wayne A. Noda, Stephen Graham Bell, "Devices and Methods for Securing Tissue", related U.S. Appl. No. 14/043,038, Non-Final Office Action dated Apr. 11, 2016.

Wayne A. Noda, Stephen Graham Bell, "Devices and Methods for Securing Tissue", related U.S. Appl. No. 14/043,038. Applicant's response to Non-Final Office Action, filed Apr. 12, 2016.

* cited by examiner

DELIVERY ASSEMBLY FOR RESILIENT TISSUE CLAMP

FIELD

The present application relates generally to devices and methods for securing tissue.

BACKGROUND

Internal body tissue sometimes must be secured together for various reasons. As an example, diverticulosis is an unfortunately common condition in which an area of the intestine bulges out into the peritoneal cavity to form a sac referred to as a "diverticulum". The present assignee has provided, in U.S. Pat. No. 8,062,308 (incorporated herein by reference), a natural orifice method for resolving diverticulum by inverting them and then securing opposed serosal surfaces together using a ring to thereby tightly and securely close off the affected tissue to alleviate the risk of peritonitis.

SUMMARY

As understood herein, it would be advantageous to provide a delivery assembly to facilitate accurate and easy delivery of the ring onto the target tissue and that could employ an off the shelf endoscope to do so without requiring manufacturer modification of the endoscope.

Accordingly, a delivery assembly for a tissue compression ring includes a sleeve that fits snugly over a main endoscope over a distal end of the endoscope. A carrier projects distally away from the sleeve and is configured for carrying one or more resilient tissue compression rings in a stretched configuration. A push ring is slidably disposed on the carrier, and at least one actuator is connected to the push ring. The actuator extends through the carrier, around a distal end of the carrier, and to the push ring to connect thereto such that when the actuator is pulled proximally, the push ring is urged distally on the carrier to push at least one compression ring off the carrier, at which point the compression ring is relaxed to assume a small configuration and clamp target tissue. The actuator can include at least a distal segment made of a flat ribbon.

In some examples, the actuator has a proximal segment made of a cable, wire, or string, and the proximal segment is connected to the distal segment. The cable, wire, or string can have a circular cross-section.

In examples, plural co-parallel longitudinal grooves are formed in the carrier to receive respective nodules on an inside surface of the push ring. The same or different co-parallel longitudinal grooves can also be used to accept spikes on the compression ring.

If desired, a rotatable take up mechanism can be engaged with a proximal segment of the actuator and rotatable by hand to wind the actuator and thereby move the push ring. The take up mechanism can include a slip feature to limit torque applied to the take up mechanism. In one example, the slip feature includes at least one detent. In another example, the slip feature includes at least one magnet.

In another aspect, an assembly for adapting an endoscope for delivery of a tissue compression ring defining a central ring axis passing perpendicularly through an opening of the tissue compression ring includes an engagement member connectable to a distal portion of the endoscope. At least one cylinder is coupled to the engagement member and is configured to hold at least one compression ring on an outer surface of the cylinder. At least one push ring is slidably coupled to the cylinder and is connected to at least one actuator that bends around a distal end of the cylinder such that pulling a proximal segment of the actuator urges the push ring distally on the cylinder.

Also disclosed is a take up mechanism for a medical device actuator which includes a bracket and a hollow tube extending through the bracket. The tube is configured to engage a proximal entry of a channel of a medical device, with the actuator extending through the tube into the channel. A spool is supported by the bracket, and the actuator is windable on the spool. A hand wheel is coupled to the spool and is rotatable by a person to rotate the spool to pull the actuator, and a slip feature may be associated with the hand wheel to limit torque applicable to the spool by means of the hand wheel.

The slip feature can include at least one detent. In turn, the detent may include at least one ball disposed on an end of at least one radially-oriented spring disposed in a channel of an inner wheel. The ball is urged by the spring into a concavity of an outer wheel surrounding the inner wheel. In this way, the inner wheel is coupled to the outer wheel by the detent so that the inner wheel turns along with the outer wheel when torque applied to the outer wheel does not exceed a threshold. However, when torque applied to the outer wheel exceeds the threshold, the ball slips out of the concavity to enable the inner wheel to rotate relative to the outer-wheel.

In addition or alternatively, the slip feature may include at least one magnet. In this embodiment, the hand wheel can include an outer wheel including at least one outer magnet and a coupling including at least one inner magnet facing a radially oriented face of the outer magnet. The inner magnet attracts the outer magnet to couple the coupling to the outer wheel to rotate therewith only so long as torque applied to the outer wheel does not exceed a threshold.

The details of the present application, both as to its structure and operation, can best be understood in reference to the accompanying drawings, in which like reference numerals refer to like parts, and in which:

DETAILED DESCRIPTION

Figure 1:
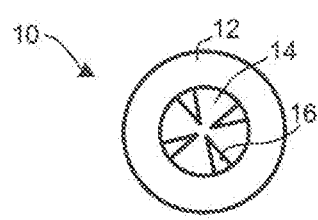
FIG. 1 is a plan view of an example compression ring according to present principles.
Figure 2:
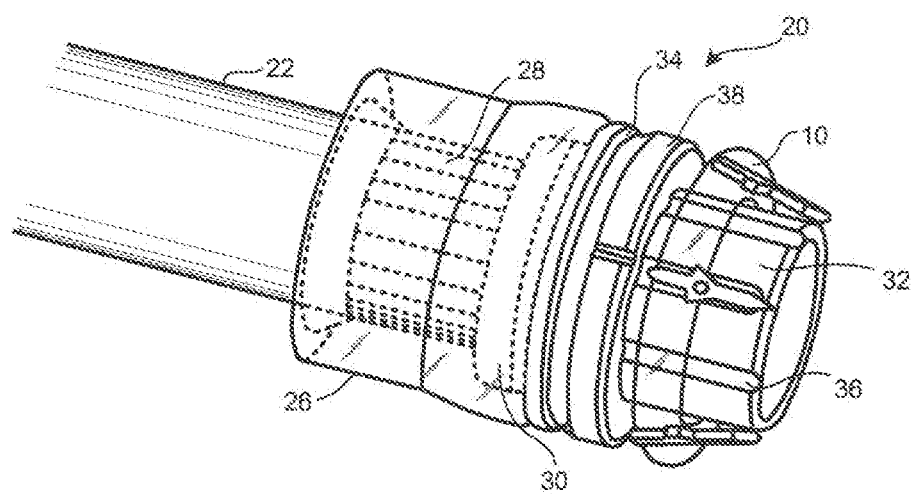
FIG. 2 is a perspective view of the delivery assembly showing the ring on the assembly with spikes oriented distally and showing portions of the assembly transparently to reveal interior structure, with the push ring in the retracted position, with proximal portions of the endoscope broken away.
Figure 3:
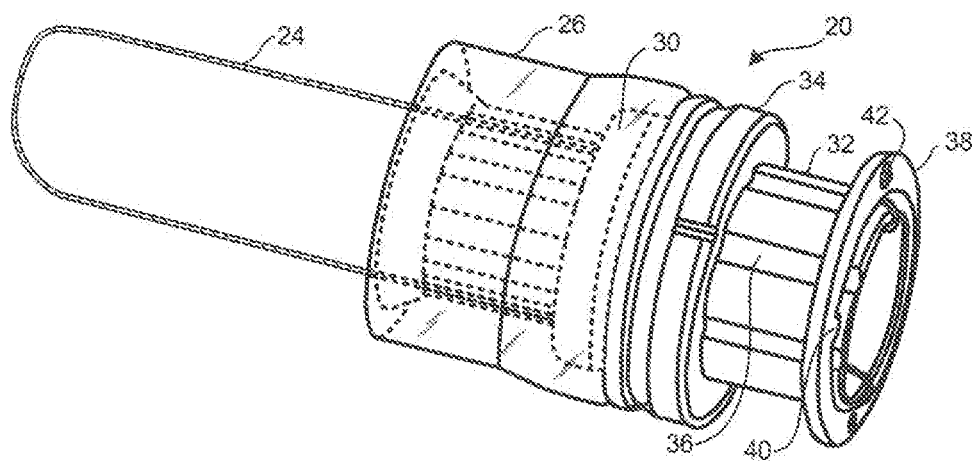
FIG. 3 is a perspective view of a first embodiment of the delivery assembly with the endoscope removed for clarity, showing the push ring in the extended position.
Figure 4:
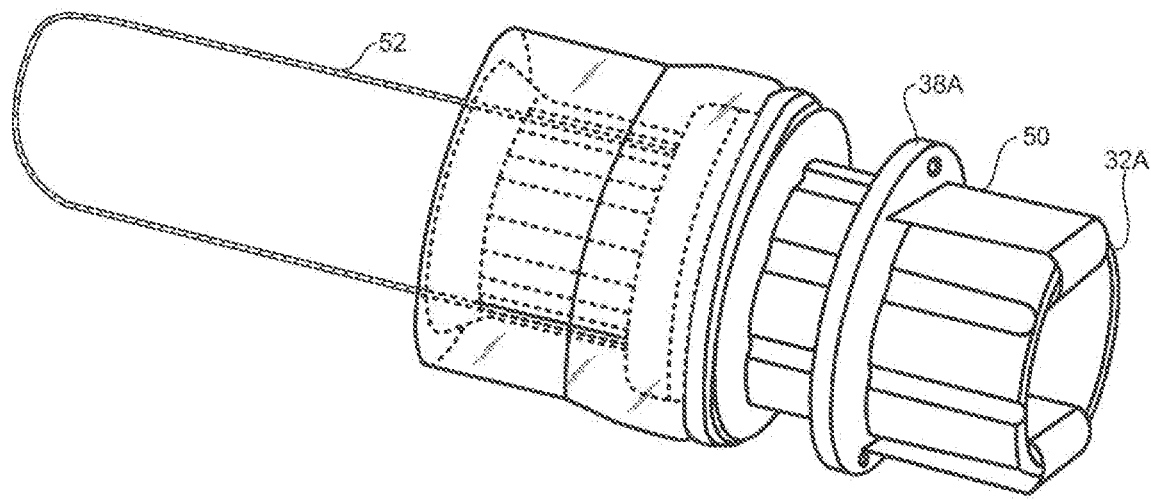
FIG. 4 is a perspective view of a second embodiment of the delivery assembly with the endoscope removed for clarity, showing the push ring between the retracted and extended position, in which the distal segments of the actuator are established by flat ribbons.

Referring initially to FIG. 1, an example non-limiting compression ring 10 is shown that may be used in connection with the delivery assembly shown in FIGS. 2-4. It is to be understood that other compression rings may be used, e.g., any suitable rings shown and described in the above-referenced patent, and that the ring in FIG. 1 is exemplary only. For example, any of the compression rings shown in U.S. Pat. Nos. 8,647,352 and 9,125,656, incorporated herein by reference, can be used.

As shown, the ring 10 includes a toroidal resilient hollow body 12 defining a compression channel 14. Four tissue spikes 16 are embedded in the body 12 and are equidistantly radially spaced from each other, extending into the compression channel 14 with the ends of the spikes 16 meeting substantially in the center (axis) of the channel.

In a relaxed state, the ring 10 assumes a radially smaller configuration, and is resilient so that it can be stretched to a radially enlarged state to fit onto the carrier described below. The body 12 can be plastic or rubber and may contain a drug eluting material. The body 12 may be coated with and then elute drugs such as antiinflammatories, antibiotics, antibacterial drugs, and tissue healing factors. The drug coating can include a bioabsorbable polymer that is loaded with the drug that releases over time.

In one implementation, for example, the body 10 and/or gripping elements such as spikes may be coated with a polymer such as Polyglycolic-Lactic Acid (PGLA) layers. The layers may be, e.g., bonded to the spikes. The PGLA can be loaded with a carrier drug that elutes as the PGLA absorbs. PGLA can be solubilized in a vapor form by dissolving it in a solvent such as, e.g., dimethyl formamide (DMF). This composition can then have the required drug added, and then sprayed in layer coatings onto the spike or the body. The dosage can be by weight. Furthermore, antimicrobials, anti-inflamatories, heavy weight proteins such as tissue growth factors, etc. may also be mixed into the composition to help with wound healing. The drug eluting coating can be applied with no primer and then heat set onto the spikes or ring.

With this in mind, it may be appreciated that when the compression ring is pushed off the delivery device onto, e.g., a diverticulum, the ring collapses around the diverticulum as the ring assumes the relaxed configuration, with the diverticulum captured and compressed in the compression channel 14. Furthermore, owing to its material bias the ring 10 twists about its circumference into the relaxed configuration, wherein the spikes/gripping elements 16 extend perpendicularly to the compression channel 14, penetrating the tissue owing to the hoop strength of the compression ring.

FIGS. 2 and 3 show a delivery assembly 20 for delivering the tissue compression ring 10. In FIG. 2 the ring 10 is stretched onto the assembly 20 with the engagement members (spikes) 16 oriented distally.

As shown in FIG. 2, the assembly 20 is engageable with an endoscope 22. The endoscope 22 may contain several channels. In the example shown, the endoscope 22 includes a camera lens which, via fiber optics, sends images back through a fiber lumen in the endoscope 22 to a display assembly external to a patient for viewing of images within the patient by a medical caregiver. The example non-limiting endoscope 22 also may include one or more illumination sources such as light emitting diodes (LED), which receive power through a lead extending through a lead lumen in the endoscope. Fiberoptic light sources may also be used. Also, the endoscope 22 may include an irrigation lumen through which irrigating fluid such as water or saline may be directed onto tissue, A lens cleaner may also be provided.

In addition, a working channel may be formed in the endoscope 22, and a typically flexible actuator such as a metal or plastic of fiber cable or wire or string 24 (FIG. 3) positioned in the working channel to extend out of the proximal end of the endoscope so that it can be manipulated by a person for purposes to be shortly disclosed. The working channel can be connected to a source of vacuum to draw tissue into the below-described delivery assembly. The cable or wire or string 24 typically has a round cross-section or otherwise a cross-section that is not necessarily wider in one dimension than another.

Having described the endoscope 22, attention is now turned to the delivery assembly 20. A cylindrical resilient or elastic rubber or plastic sleeve 26 fits snugly over the distal end segment 28 (shown in FIG. 2 inside the partially transparent sleeve) of the endoscope 22 as shown. The sleeve 26 is hollow and cylindrical and may substantially completely surround the endoscope in a tight friction or press fit, so that a person can engage the sleeve 26 with the distal segment of the endoscope by hand by simply sliding the sleeve onto and past the distal end 30 (which in FIGS. 2 and 3 is established by an annular collar having a larger diameter than the rest of the endoscope) of the endoscope. In other embodiments the collar depicted at 30 in FIGS. 2 and 3 may be made integrally with the hollow cylinder described below.

Owing to the snug fit between the inner surface of the sleeve 26 and the outer surface of the endoscope 22, the sleeve remains in the position shown in FIGS. 2 and 3 until such time as a person employs sufficient force to pull the sleeve off the endoscope. However, in some embodiments the sleeve may be bonded or otherwise more tightly affixed to the endoscope to prevent a person from pulling the sleeve off the endoscope.

As shown in FIGS. 2 and 3, distal to and coaxial with the sleeve 26 is a hollow delivery cylinder 32, which may be made of hard plastic or other suitable material. The cylinder 32 may be glued or otherwise connected to the sleeve 26. A proximal stop flange 34 may be formed integrally around the open proximal end of the cylinder 32 as shown. The stop flange 34 may be part of the cylinder 32 that is bonded to or otherwise attached to the sleeve 26. Multiple longitudinal grooves 36, each of which may be parallel to the long axis of the cylinder 32, may be formed on the exterior of the cylinder 32 and may be parallel to each other and separated from each other by, e.g., fifteen degrees of angular difference relative to the axis of the assembly, although a smaller or larger spacing may be used.

Figure 9:
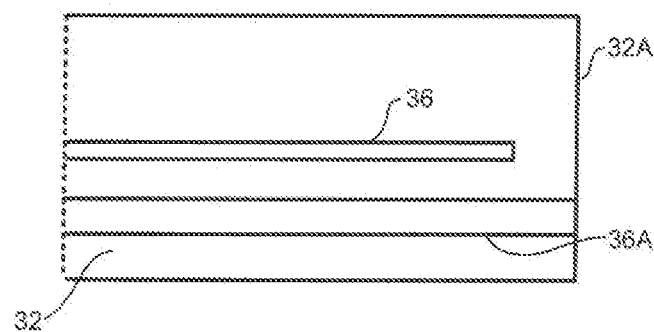
FIG. 9 is a schematic side view of as example delivery cylinder showing two types of longitudinal grooves, one to accept structure in the push ring and one to accept structure in the compression ring.

In addition to aligning the push ring as described below, the grooves may be spaced to register with the spikes on the compression ring to accept respective spikes during deployment. Or, referring briefly to FIG. 9, different longitudinal grooves 36A may be formed between the push ring grooves 36 to accept spikes on the compression ring 10. When respective different grooves 36A, 36 are provided for the compression ring 10 and the push ring, the grooves 36 for the push ring may terminate just before the distal end 32A of the cylinder 32 to ensure the push ring cannot slip off the distal end, whereas the grooves 36A for the compression ring spikes extend all the way to the distal end 32A of the cylinder 32 to facilitate the compression ring sliding off the cylinder.

The spikes may be pre-loaded onto the cylinder 32 oriented proximally as described in U.S. Pat. No. 8,647,352, incorporated by reference above.

As alluded to above, a push ring 38, which may be made of rigid plastic, is slidably engaged with the cylinder 32 for movement between the retracted position shown in FIG. 2, in which the push ring 38 substantially abuts the proximal stop flange 32 to make room for one or more compression rings 10 to be mounted on the cylinder 32 distal to the push ring 38, and an extended position as shown in FIG. 3, in which the push ring is moved distally to substantially the distal end of the cylinder 32 to push compression rings off of the cylinder, at which point the compression ring 10 relaxes, through material bias, to assume a small configuration and clamp target tissue. The endoscope, cylinder 32, and push ring 38 are all coaxial in the example shown in FIGS. 2 and 3.

The push ring 38 is hollow and on its inside surface may be formed with one or more round nodules 40 (best shown in FIG. 3) that are registered with respective grooves 36 in the cylinder, so that the push ring 38 is prevented from rotating on the cylinder 32 as it slides on the cylinder owing to the nodules 40 being confined within their respective grooves 36. Note that when the grooves 36 are tailored specifically for the nodules 40, as discussed above the grooves 36 can terminate just before the distal end of the cylinder 32. In such an embodiment, the push ring can have a one way snap on fit for assembly.

The actuator 24, as can best be appreciated in reference to FIG. 3, extends through the endoscope and cylinder 32 and out of the distal end of the cylinder 32, wrapping around the distal end back proximally to engage the push ring 38. In one embodiment, two segments of the actuator 24 extend through the cylinder 32 and engage the push ring 38 at diametrically opposite locations. In the specific example shown, each end of the actuator 24 extends back under the push ring 38, i.e., between the push ring 38 and the cylinder 32, and then is engaged with a respective hole 42 in the push ring 38. The actuator ends may be glued or otherwise secured to the push ring 38.

It may now be appreciated that with the sleeve 26 surrounding the endoscope 22 to engage the cylinder 32 with the endoscope, the push ring 38 can be moved by hand to the retracted position of FIG. 2. One or more compression rings 10 may then be loaded onto the cylinder 32. When the endoscope is advanced as appropriate near target tissue, the actuator 24 can be pulled proximally, which draws the push ring 38 distally toward the extended position shown in FIG. 3, urging one or more compression rings 10 off the cylinder 32 onto target tissue.

Figure 5:
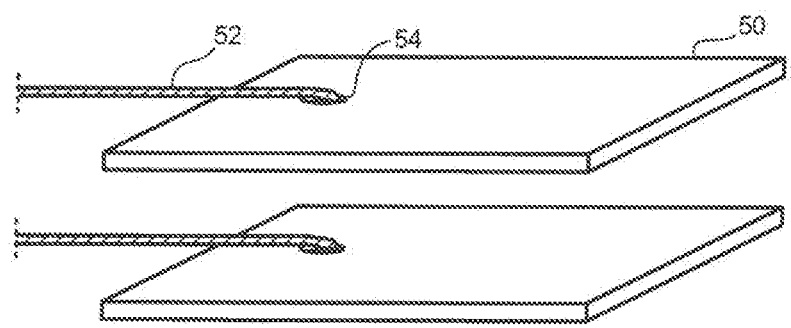
FIG. 5 is a perspective view of the actuator of FIG. 4 before attaching the distal ribbons to the push ring, with proximal ends of the cord broken away.

FIGS. 4 and 5 show and alternate embodiment with a cylinder 32A engageable with a sleeve 26A for engagement with an endoscope and with a slidable push ring 38A on the cylinder 32A according to description above. Unlike the embodiment of FIGS. 2 and 3 however, in FIGS. 4 and 5 the distal end segments of the two actuator segments are flat flexible ribbons 50 made of, e.g., low-friction flexible plastic. Example non-limiting materials that may be used for the ribbons include thin polytetrafluoroethylene (PTFE) and ultra high molecular weight (UHMW) plastic such as UHMW polyethylene. In any case, as shown best in FIG. 5 each ribbon 50 is significantly wider than it is thick, and when laid flat is shaped as a flat parallelepiped.

Each ribbon 50 may be connected to a respective proximal segment 52 of the actuator, such as a cord as described above, by, e.g., threading the cord through a hole 54 in the ribbon and/or otherwise bonding or otherwise engaging the cord with the ribbon.

As understood herein, using relatively wide flat ribbons, which wrap back around the distal end of the cylinder between the cylinder and the compression rings, reduces the surface area of contact between the cylinder 32A and the compression rings, reducing the friction resisting pushing the compression rings off the assembly and thus reducing the amount of tensile force that must he applied to the actuator to move the push ring 38A.

Figure 6:
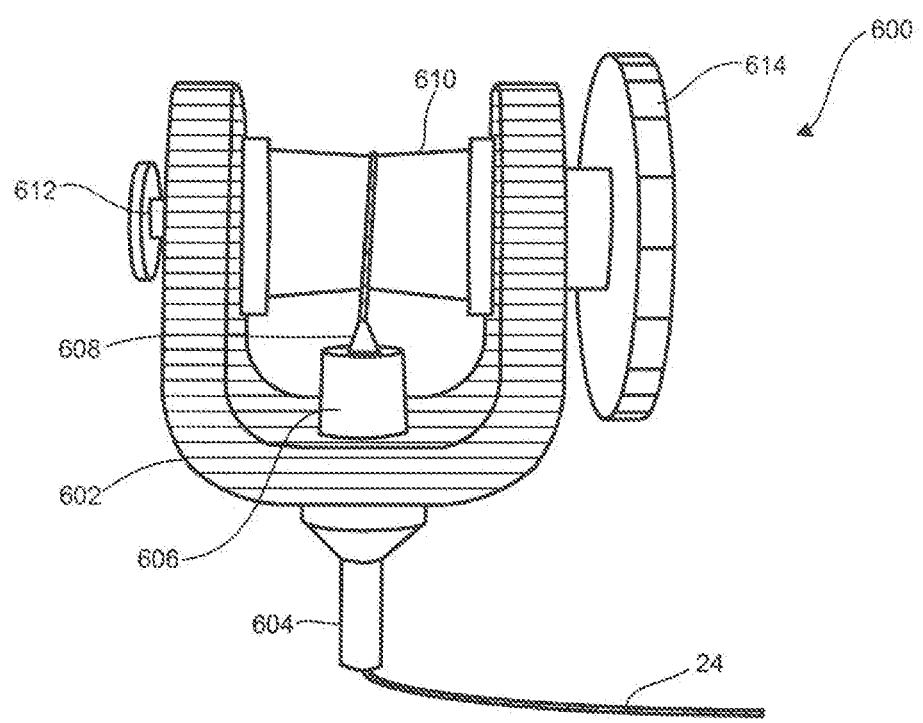
FIG. 6 is a perspective view of a take up mechanism that can be used to tension the actuator to move the push ring.

Now refer to FIG. 6 for an example take up mechanism 600 that may be used by a caregiver to tension the actuator 24. The mechanism 600 includes a rigid metal or plastic bracket 602 that is shaped as a flat "U" as shown, with a hollow tube 604 extending through the bottom (proximal-most) segment of the bracket 602 as shown. The tube may be stainless steel, and is configured to engage a proximal entry of a working channel of the endoscope shown in FIG. 2 in an interference fit if desired. The proximal portion of the actuator 24 extends through the tube 604 and can feed out of the tube through a neck-down fitting 606 that is engaged coaxially with the tube 604 and that has an exit port 608 with a diameter only marginally larger than the diameter of the actuator 24 as shown. This latter structure may be established at least in part by an elastomeric duckbill valve that seals around the actuator 24 to provide vacuum tightness for inverting tissue.

After exiting the exit port 608, the actuator 24 winds around a spool 610 that is mounted between the opposed arms of the bracket 602 onto an axle 612 that extends between the arms of the bracket. A hand wheel 614 is coupled to the spool 610 so that a person can rotate the hand wheel to rotate the spool 610 around the axle 612 to pull the actuator 24 proximally. That is, the actuator 24 is wrapped around the spool 610 so rotational torque imposed on the spool 610 is converted into linear tension on the actuator 24.

As understood herein, when turning the hand wheel 614 to pull on the actuator 24, it is possible to exert a very large amount of force that can undesirably contort the endoscope, which typically is flexible, and potentially cause harm to the instrument and the patient. Accordingly, the take up mechanism 600 preferably includes a slip feature to limit torque applied to the take up mechanism, which will limit the amount of linear tension that the actuator 24 experiences.

Figure 7:
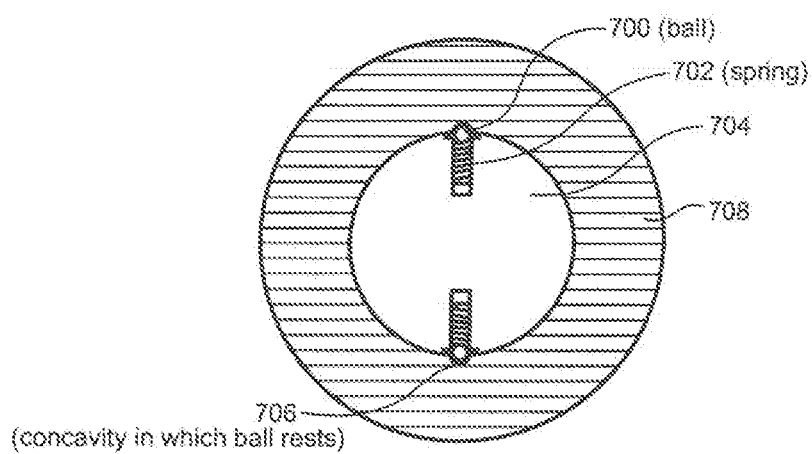
FIG. 7 is a side cut-away view showing a detent-based slip feature that can be used to limit the torque applied while using the take up mechanism of FIG. 6 and, hence, to limit the tensile stress that can be imposed on the actuator.

FIG. 7 illustrates a first embodiment of a slip feature that uses detents established by respective rigid balls 700 disposed at the outer ends of respective radially-oriented springs 702 which compress at a desired amount of force. In the example shown, the hand wheel 614 of FIG. 6 includes an inner wheel 704 that is connected to the axle 612 or spool 610 of FIG. 6. The springs 702 are disposed in respective radially-oriented channels in the inner wheel, and the balls 700 rest in respective concavities 706 formed in the inner surface of a hollow outer wheel 708, which also forms part of the hand wheel 614 in FIG. 6. The inner wheel 704 is thus coupled to the outer wheel 708 by means of the detents so that the inner wheel 704 turns along with the outer wheel 708, so long as torque applied to the outer wheel remains below a threshold.

When the torque on the outer wheel 708 exceeds the threshold, however, the balls 700 on the end of the springs 702 cannot maintain engagement with their respective concavities, slipping out and thus against the inner surface of the outer wheel 708. This enables the inner wheel 704 to spin freely inside of the outer wheel 708 and no greater torque can be applied to the spool.

Figure 8:
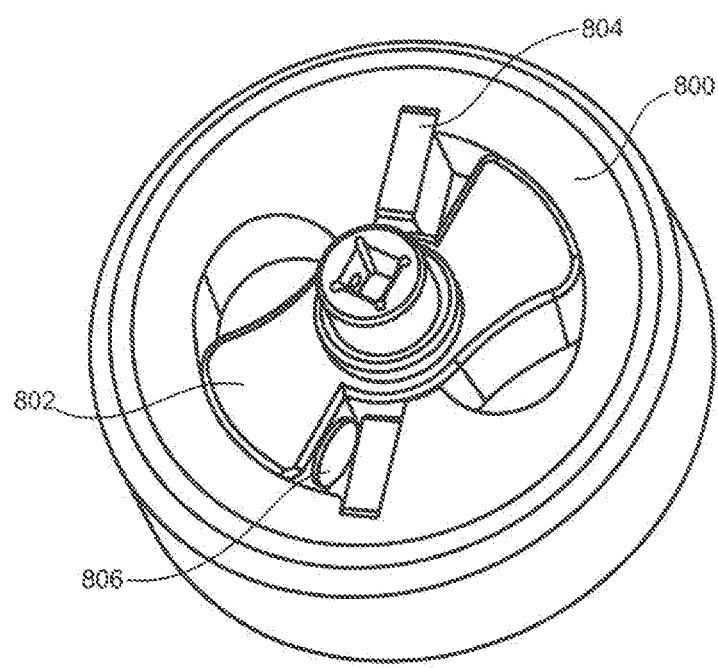
FIG. 8 is a side cut-away view showing a magnet-based slip feature that can be used to limit the torque applied while using the take up mechanism of FIG. 6 and, hence, to limit the tensile stress that can be imposed on the actuator.

FIG. 8 shows a slip feature that is based on magnetism. The hand wheel 614 in FIG. 6 may be established by a hollow outer wheel 800 that closely receives a coupling 802 that is connected to the axle or spool of FIG. 6. In the example shown, first and second outer magnets 804 are oriented lengthwise in the radial dimension as shown, diametrically opposed to each other. Each outer magnet 804 can be received in a respective channel formed in the inner surface of the hollow outer wheel 800 as shown. If desired, the magnets 804 may be bonded to the outer wheel 800.

Each outer magnet 804 faces a respective inner magnet 806 that is attached to (e.g., by bonding) to the coupling 802. In the example shown, the inner magnet is azimuthally offset from its respective outer magnet, with the major faces of the inner and outer magnets disposed along the radial dimension. The faces of the inner magnets that face the outer magnets are of the opposite polarity than the faces of the outer magnets facing the respective inner magnets, so that each inner magnet-outer magnet pair attracts to couple the coupling 802 to the outer wheel 800 to rotate with the outer wheel 800 so long as torque applied to the outer wheel 800 does not exceed a threshold.

When, however, the torque applied to the outer wheel exceeds the threshold, the magnetic coupling between the outer wheel 800 and coupling 802 is broken so that the coupling 802 no longer rotates with the outer wheel 800. That is, once the torque threshold is reached, the inner magnets 806 separate from their respective outer magnets 804 and the outer wheel 800 thus disconnects from the axle/spool shown in FIG. 6 to spin freely, transmitting no further torque to the axle/spool.

While the particular DELIVERY ASSEMBLY FOR RESILIENT TISSUE CLAMP is herein shown and described in detail, it is to be understood that the subject matter which is encompassed by the present invention is limited only by the claims. Components included in one embodiment can be used in other embodiments in any appropriate combination. For example, any of the various components described herein and/or depicted in the Figures may be combined, interchanged or excluded from other embodiments.

What is claimed is:

1. An assembly for adapting an endoscope for delivery of a tissue compression ring defining a central ring axis passing perpendicularly through an opening of the tissue compression ring, the assembly comprising:
    an engagement member connectable to a distal portion of the endoscope;
    at least one cylinder coupled to the engagement member and configured to hold at least one tissue compression ring on an outer surface of the cylinder;
    at least one push ring slidably coupled to the cylinder, said at least one push ring being provided around the outer surface of the cylinder and connected to at least one actuator that bends around a distal end of the cylinder such that pulling a proximal segment of the actuator urges the at least one push ring and a tissue compression ring adjacent to the at least one push ring distally on the cylinder; and
    plural co-parallel longitudinal grooves in the cylinder to receive respective structure on the at least one push ring, said grooves in the cylinder terminating before the distal end of the cylinder.

2. The assembly of claim 1, comprising a rotatable take up mechanism engaged with a proximal segment of the actuator and rotatable by hand to move the at least one push ring, the take up mechanism including a slip feature to limit torque applied to the take up mechanism.

3. The assembly of claim 1, said at least one push ring being made of rigid plastic.

* * * * *